US011252985B1

(12) United States Patent
Yiannios (10) Patent No.: US 11,252,985 B1
(45) Date of Patent: Feb. 22, 2022

(54) DIETARY SUPPLEMENT COMPOSITIONS INCLUDING CANNABIDIOL FORMULATIONS HAVING ENHANCED BIOAVAILABILITY WITH SUSTAINED TIME RELEASE AND ENHANCED ORGANOLEPTICS, AND METHODS OF MAKING SAME

(71) Applicant: CANNASPHERE BIOTECH, LLC, Gilbert, AZ (US)

(72) Inventor: James John Yiannios

(73) Assignee: Cannasphere Biotech, LLC., Gilbert, AZ (US)

(*) Notice: Subject to any disclaimer, the term of this patent is extended or adjusted under 35 U.S.C. 154(b) by 142 days.

(21) Appl. No.: 16/428,267

(22) Filed: May 31, 2019

Related U.S. Application Data (60) Provisional application No. 62/678,608, filed on May 31, 2018.

(51) Int. Cl.
*A23L 33/105* (2016.01)
*A61K 31/05* (2006.01)
(Continued)

(52) U.S. Cl.
CPC .......... *A23L 33/105* (2016.08); *A23L 33/125* (2016.08); *A61K 9/1277* (2013.01); *A61K 31/05* (2013.01); *A61K 36/185* (2013.01); *A61K 47/24* (2013.01); *A61K 47/26* (2013.01); *A61K 47/40* (2013.01); *A61K 47/46* (2013.01);
(Continued)

(58) Field of Classification Search
CPC ... A23L 33/125; A23L 33/105; A61K 9/1277;
A61K 31/05; A61K 36/185; A61K 47/24;
A61K 47/26; A61K 47/40; A61K 47/46;
A23V 2002/00; A23V 2002/30; A23V 2250/1842; A23V 2250/21;
(Continued)

(56) References Cited

FOREIGN PATENT DOCUMENTS

CA 3020616 A1 * 10/2017
CN 105916492 A * 8/2014
(Continued)

*Primary Examiner* — Helen F Heggestad
(74) *Attorney, Agent, or Firm* — Carrier Blackman & Associates, P.C.; Joseph P. Carrier; Fulchand P. Shende (57) ABSTRACT

A dietary supplement composition has a dispersion including a plurality of liposomal vesicles. The dietary supplement composition includes an active ingredient including one or more hydrophobic nutrient, such as cannabinoid or cannabinoid compound (cannabinoid), and phospholipid contained in the liposomal vesicles. The cannabinoid, which may be combined with cyclodextrin, is incorporated within the liposomal vesicles. The dietary supplement composition may further include one or more of rice bran extract, mannitol and trehalose. A method of preparing such dietary supplement composition includes generating a cannabinoid phase, generating an phospholipid phase, adding the cannabinoid phase and the phospholipid phase in vessel; performing a homogenizing step by mixing the cannabinoid phase and the phospholipid phase so as to form a cannabinoid-phospholipid composition having a plurality of liposomal vesicles having the cannabinoid incorporated therein, wherein the concentration of cannabinoid in the cannabinoid-phospholipid composition is about 10 to 25 mass %.

18 Claims, 6 Drawing Sheets

(51) Int. Cl.
*A61K 9/127* (2006.01)
*A61K 47/24* (2006.01)
*A61K 47/40* (2006.01)
*A61K 47/46* (2006.01)
*A61K 47/26* (2006.01)
*A23L 33/125* (2016.01)
*A61K 36/185* (2006.01)

(52) U.S. Cl.
CPC ....... *A23V 2002/00* (2013.01); *A23V 2200/30* (2013.01); *A23V 2250/1842* (2013.01); *A23V 2250/21* (2013.01); *A23V 2250/5112* (2013.01); *A23V 2250/636* (2013.01); *A23V 2250/6418* (2013.01)

(58) Field of Classification Search
CPC ...... A23V 2250/5112; A23V 2250/636; A23V 2250/6418
USPC ......................... 426/648, 615, 601, 662, 519
See application file for complete search history.

(56) References Cited

FOREIGN PATENT DOCUMENTS

| | | | |
|---|---|---|---|
| CN | 105916492 | * | 8/2016 |
| WO | WO2017/177261 | * | 10/2017 |

* cited by examiner

DIETARY SUPPLEMENT COMPOSITIONS INCLUDING CANNABIDIOL FORMULATIONS HAVING ENHANCED BIOAVAILABILITY WITH SUSTAINED TIME RELEASE AND ENHANCED ORGANOLEPTICS, AND METHODS OF MAKING SAME

CROSS-REFERENCE TO RELATED APPLICATIONS

The present application claims priority under 35 USC 119 based on U.S. Provisional patent application No. 62/678,608, filed on May 31, 2018. The entire subject matter of this priority document, including specification claims and drawings thereof, is incorporated by reference herein.

BACKGROUND OF THE INVENTION

1. Field of the Invention

The present invention relates to dietary supplement compositions including cannabidiol (hereinafter referred to as Hemp CBD, hemp-derived CBD or as CBD) formulations having enhanced bioavailability with sustained time release and enhanced organoleptics, and methods of making same. More particularly, the present invention relates to dietary supplement compositions including an instantized water soluble liposomal CBD formulation, such as powder or emulsion, in which CBDs are incorporated in liposomal vesicles, having enhanced bioavailability with sustained time release and enhanced organoleptics, and methods of making same.

2. Background Art

It is known that cannabidiol is hydrophobic compound that is acid-labile. Because of its hydrophobic nature, cannabinoids are poorly absorbed systemically from oral dosage forms in the aqueous environment of the gastrointestinal tract, and oral formulations of cannabinoids, therefore, exhibit low bioavailability. Disadvantages of oral ingestion (oil drops, capsules, tea) include slow and insufficient absorption, delayed onset of action and low systemic bioavailability. The present invention has been made to overcome such drawbacks.

SUMMARY OF THE INVENTION

In order to achieve the above objects, the present invention provides a dietary supplement composition including a stable, liposome encapsulation with time release characteristics and enhanced organoleptic properties of cannabinoids, or mixtures of cannabinoids (derived from Hemp), cyclodextrin and sunflower lecithin rich in phosphatidylcholine that is suitable for nutraceutical application. Cyclodextrin may be optional in some formulations as discussed herein. Also provided is a method for the manufacture of liposomal encapsulation of CBD that has enhanced shelf life free of excipients and solvents.

The present invention overcomes the drawbacks described above by providing a stable liposomal composition in the form of instantized powder. The composition of the liposome can range between 10%-35% provided the phosphatidylcholine is at least 50% of the total phospholipids.

According one aspect of the present invention, the dietary supplement composition having a dispersion includes a plurality of liposomal vesicles, a hydrophobic nutrient including at least one of cannabinoid and mixtures of cannabinoids; and phospholipid contained in the liposomal vesicles. The hydrophobic nutrient is incorporated within the liposomal vesicles. One of a microfluidizer and a homogenizer is used for generating the dispersion which includes the hydrophobic nutrient is in the amount of about 10-25 mass %, preferably 20 mass % or more.

According to another aspect of the present invention, a method of preparing the dietary supplement composition includes the method steps of generating a cannabinoid phase by inclusion of cyclodextrin (preferably β-cyclodextrin, but types of cyclodextrins may be used) thereby creating cyclodextrin-CBD inclusion and by stirring the cyclodextrin-CBD inclusion in distilled water in first container; generating a phospholipid phase by stirring a phospholipid compound, such as sunflower lecithin/sunflower lipid (PC), in distilled water in second container; adding the cannabinoid phase and the phospholipid phase in vessel; performing a homogenizing step by mixing said cannabinoid phase and the phospholipid phase using a microfludizer (high pressure homogenization) at a temperature of about 55-65° C. so as to form a cannabinoid-phospholipid composition having a plurality of liposomal vesicles of the phospholipid, the liposomal vesicles having the cyclodextrin-CBD inclusion incorporated therein. In such composition, the concentration of CBD is in the range of about 10-25%, preferably about 20% or more. In other words, preferable ratio of concentration of CBD to the dietary supplement composition is about 1:5 or more.

For a more complete understanding of the present invention, the reader is referred to the following detailed description section, which should be read in conjunction with the accompanying drawings.

DETAILED DESCRIPTION OF ILLUSTRATIVE EMBODIMENTS

The present invention provides dietary supplement compositions and methods of preparing dietary supplement compositions for producing stable CBD formulations of hemp rich phyto cannabinoids. In other words, CBD formulations of present invention include hemp-derived CBD. Several embodiments of preparing dietary supplement compositions are discussed.

First Embodiment

In the first embodiment, the main materials/ingredients used are (1) CBD, (2) cyclodextrin, (3) distilled water, (4) sunflower lecithin, and (5) one or more of rice bran, mannitol and trehalose. Thus, according to the first embodiment, the dietary supplement composition includes (1) CBD, (2) cyclodextrin, (3) distilled water, (4) sunflower lecithin, and (5) one or more of rice bran, mannitol and trehalose. CBD used in the formulations is in oil form. Powder form of CBD may be used.

Figure 1:
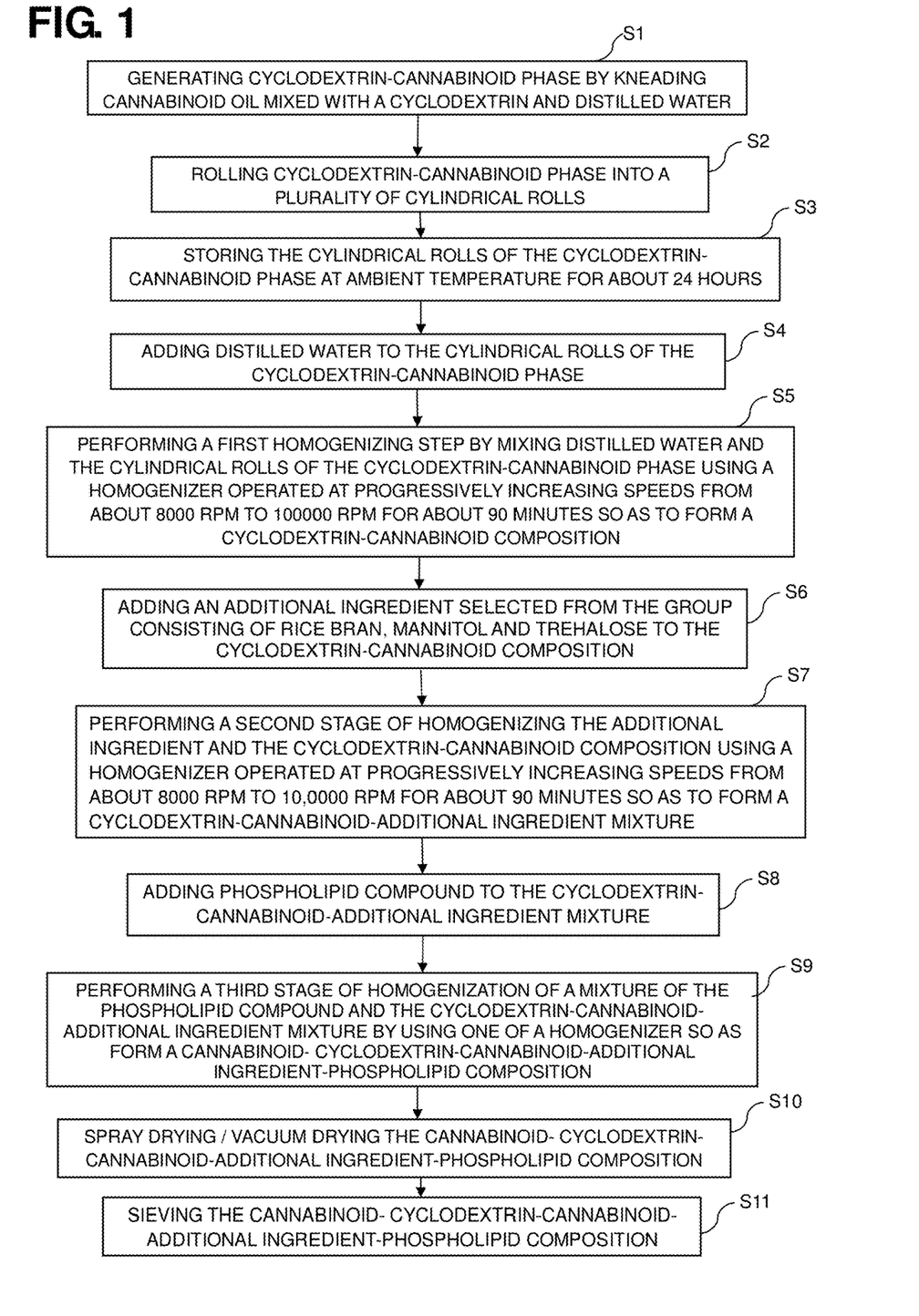
FIG. 1 is a flowchart showing method steps of preparing a dietary supplement composition according to a first embodiment of the present invention.

The method of preparing a dietary supplement composition according to a first embodiment includes several steps as shown in FIG. 1. The method steps for preparing a dietary supplement composition according to the first embodiment are:

(1) generating cyclodextrin-cannabinoid phase by incorporating cannabinoid oil in beta cyclodextrin to obtain a dough like cannabinoid paste, the CBD is kneaded with the cyclodextrin, for example, beta cyclodextrin (β-CD) and a small amount of distilled water for about three hours to maintain a suitable consistency of paste (STEP S1);

(1a) rolling the paste (cyclodextrin-cannabinoid phase) into cylindrical rolls (STEP S2);

(1b) storing cylindrical rolls for about 24 hours at ambient temperature (STEP S3);

(2) incorporating the beta cyclodextrin-cannabinoid phase in distilled water to obtain a water-soluble beta cyclodextrin-cannabinoid base, or adding distilled water to the cylindrical rolls (STEP S4), (2a) performing first homogenizing step by mixing distilled water and the water-soluble beta cyclodextrin-cannabinoid base between 8,000-10,0000 rpm for about 90-minute increments at a temperature of about 55-65° C. (STEP S5), (3) adding an additional ingredient selected from the group consisting of rice bran extract, mannitol and trehalose to the beta cyclodextrin-cannabinoid base and blending this mixture to bind water and oil (STEP S6), (3a) performing a second stage of homogenizing the mixture of the additional ingredient (e.g., rice bran extract) and beta cyclodextrin-cannabinoid base between 8,000-10,0000 rpm in 90-minute increments at a temperature of about 55-65° C. so as to form a cyclodextrin-cannabinoid-additional ingredient mixture (STEP S7);

(4) adding a phospholipid compound, e.g., sunflower lecithin, to the above cyclodextrin-cannabinoid-additional ingredient mixture (STEP S8);

(4a) performing a third stage of homogenization by blending under high pressure homogenization or micro fluidization the cyclodextrin-cannabinoid-additional ingredient mixture and phospholipid compound so as to form the cyclodextrin-cannabinoid-additional ingredient-phospholipid composition having a plurality of liposomal vesicles whose ideal size ranges between 75 nm and 120 nm (the size of liposomal vesicles may vary between 10-120 nm, mostly in the range of 10 nm to 50 nm, with average size of about 23 nm) (STEP S9);

(5) spray drying, freeze drying or vacuum drying finished solution (STEP S10) that is further processed through a sieve (STEP S11) so as to obtain gritty powder (which may be an off white in color) that is 100% water soluble, dispersible; and reconstitutes its form when reintroduced to aqueous solution is the finished product, i.e., CBD formulation.

As a dietary composition according to the present invention any ingestible preparation that contains the finished base material can be used to make beverages, pills, tablets including edible food formats. The finished base material including powder may be used for cosmetics and tropical purposes.

As stated above, processing temperatures for homogenization of the CBD formulation are between 55-65° C. Homogenization (mixing) range is between 8,000-10,0000 rpm for steps 2 and 3 (STEPS S5 and S7 in FIG. 1) in 90-minute increments. The CBD is kneaded with the (β-CD) and small amount of distilled water for three hours to maintain a suitable consistency of paste. The paste is then rolled into cylindrical rolls and stored for 24 hours at ambient temperature. This paste is then homogenized as part of step (2) and (3). After the material is processed as part of step (5) it is put in a vacuum oven at low temperature 35-45° C. for up to 48 hours. Alternatively, it may freeze dried or spray dried. The dried complex is then passed through sieve No. 50 and stored in airtight containers till further use.

This method provides the dispersion having concentration of CBD in the range of 10%-25%, and mostly in the range of 20% to 25%. For example, 5 kg of dietary supplement composition in powder form includes about 1 kg or more of CBD (in oil form) with yield of 200,000 active CBD per kg. The methods described in other embodiments also provide similar higher yields of CBD in the composition.

A dietary supplement according to the first embodiment has a typical CBD formulation composition provided in Table 1.

TABLE 1

Example of CBD Formulation composition

| Ingredient | Amount (g) | % Activity | % |
|---|---|---|---|
| Hemp CBD (Cannabidiol) | 1 | 77.00% | 19.58% |
| βeta Cyclodextrin | 3.50 | | 68.54% |
| Sunflower Lecithin-50% PC | 0.58 | | 11.36% |
| Rice Bran Extract | 0.0267 | | 0.52% |
| Total | 5.1067 | | 100.00% |

The molecular mass of CBD is 314.464 g/mol. The ability to incorporate with βeta cyclodextrin (β-CD) which has a molecular weight 1134.987 g/mol allows us to exceed the mass by a factor of 3 to form what is referred to as an inclusion complex (see image below). The complexation constant between cannabinoids and CDs are usually in a weight ratio (dry weight to dry weight) ranging between 1:3.

Sunflower lecithin at different phosphatidylcholine (PC) levels, such as 65% to 90% may used.

Figure 7:
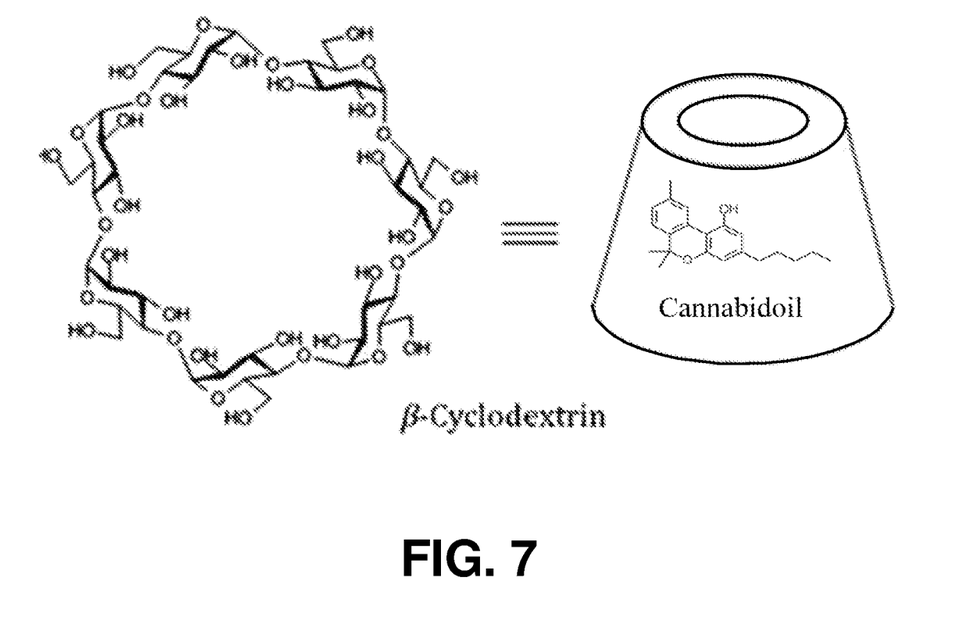
FIG. 7 illustrates a fairly rigid and well-defined hydrophobic cavities and hydrophilic rims having primary and secondary —OH groups that can be used for controlled delivery of organic, inorganic, biological and pharmaceutical molecules due to their ability to form inclusion complexes with diverse guest molecules by encapsulating the non-polar part of the guest into its hydrophobic cavity and stabilizing the polar part by the polar rims.

It may be noted that cyclodextrins (CDs) are the cyclic oligosaccharides containing six (α-CD), seven (β-CD) and eight (γ-CD) glucopyranose units, bound by α-(1-4) linkages forming a truncated conical structure. Thus because of their unique structure, i.e., fairly rigid and well-defined hydrophobic cavities and hydrophilic rims having primary and secondary —OH groups that can be used for controlled delivery of organic, inorganic, biological and pharmaceutical molecules due to their ability to form inclusion complexes with diverse guest molecules by encapsulating the non-polar part of the guest into its hydrophobic cavity and stabilizing the polar part by the polar rims as shown FIG. 7.

The cyclodextrins provides coating to liposomes (liposomal vesicles) having CBD incorporated therein.

The additional ingredient, such as rice bran extract or guar gum, helps binding any insolubilized CBD within the solution. This is incorporated with sunflower lecithin and homogenized under high pressure to form the liposomes which are then dehydrated back into a powder form for added stability and for ease of use i.e., beverage, pill and other edible products. Rice bran may be substituted or complimented with mannitol or trehalose, or both, or guar gum.

The above discussed illustrative method provides instantized, 100% water soluble liposomal CBD powder, excipient free green label—free from emulsifiers and solvents, increased bioavailability with built in time release with emphasis on safety. It may be noted that the CBD powder eliminates the need for agglomeration which removes an added step in the manufacturing process. This, in turn adds to cost savings. As discussed earlier on the poor aqueous solubility and rate of dissolution are two critical factors that affect the formulation and development process of CBD compounds and limit their therapeutic application.

The administration of actives which are poorly soluble represents a major challenge. Cyclodextrins are chemically and physically stable macromolecules produced by enzymatic degradation of starch. They are water-soluble, biocompatible in nature with hydrophilic outer surface and lipophilic cavity. They have the shape of truncated cone or torus rather than perfect cylinder because of the chair conformation of glucopyranose which are considered natural. The most common natural cyclodextrins are $\alpha$, $\beta$, and $\gamma$ consisting of 6, 7, and 8 glucopyranose units. They are crystalline, homogeneous, and nonhygroscopic substances.

Amongst these, $\beta$-cyclodextrin is ideal for complexation due to perfect cavity size, making for efficient CBD complexation and loading, availability, and it's a relatively low-cost material. The formation of inclusion complex with nontoxic agents leads to improvement in physicochemical properties of CBD and enhanced solubility and stability, as well as the bioavailability and dissolution. By creating cyclodextrin-based nanocarriers (75-120 nm) the concept of dual approach takes place as it involves combination of two different approaches in a single delivery system. This covers two aspects firstly; the CBD is complexed with suitable cyclodextrin and secondly encapsulation of complexed CBD into the carrier including liposomal vesicles.

Encapsulation of cyclodextrin complexed CBD into carriers increases the loading capacity, entrapment efficiency, prolong the existence of the CBD in systemic circulation, and reduce toxicity and provide controlled, sustained, or targeted release. Thus, the combination of cyclodextrin adds value to the product. The unique feature of optimized CBD-cyclodextrin complex when administered orally, offers tremendous safety benefits as cyclodextrins is not absorbed from gastrointestinal tract and thus becomes practically nontoxic. This is due to their bulky and hydrophilic nature. Any absorption, if it occurs, is by passive diffusion. Most of the hydrophilic derivatives of natural cyclodextrins like $\beta$-cyclodextrin as in the CBD formulation are considered safe.

In liposomes, cyclodextrin complexation competes with liposomal membrane binding, which tempers the potential benefit of complexation in prolonging hydrophobic drug retention as the entrapment of water-soluble cyclodextrin-CBD inclusion complexes in liposomes which leads to accommodation of any insoluble CBD in the aqueous phase of vesicles, increasing the CBD to lipid ratio, this enlarges the range of encapsulation, allowing targeting of complexes to specific sites, while at the same time reducing toxicity. It also allows for a reduced amount of lipid, which traditionally would not be the case.

The CBD formulation in powder form can be stored at room temperature. The liposomes in powder do not degrade at room temperature. The powder when mixed with water reconstitutes liposomes easily.

Second Embodiment

In the second embodiment, a combination of CBD and cyclodextrin is incorporated in liposomal vesicles.

In the second embodiment, the main materials/ingredients used are (1) CBD, (2) cyclodextrin, (3) distilled water, and (4) sunflower lecithin, and (5) optionally, an additional ingredient including one or more of rice bran, mannitol and trehalose.

The method of preparing the dietary supplement composition including a CBD formulation according to a second embodiment includes optimizing cyclodextrin, for example, using methyl-$\beta$-cyclodextrin at a concentration of 5 mg/mL with a short-term stability, and preparing liposomal vesicles with cyclodextrin inclusion. Cyclodextrin helps with flavor masking.

The sunflower lecithin with different phosphatidylcholine (PC) levels, for example, 50% to 90% may be used.

Figure 2:
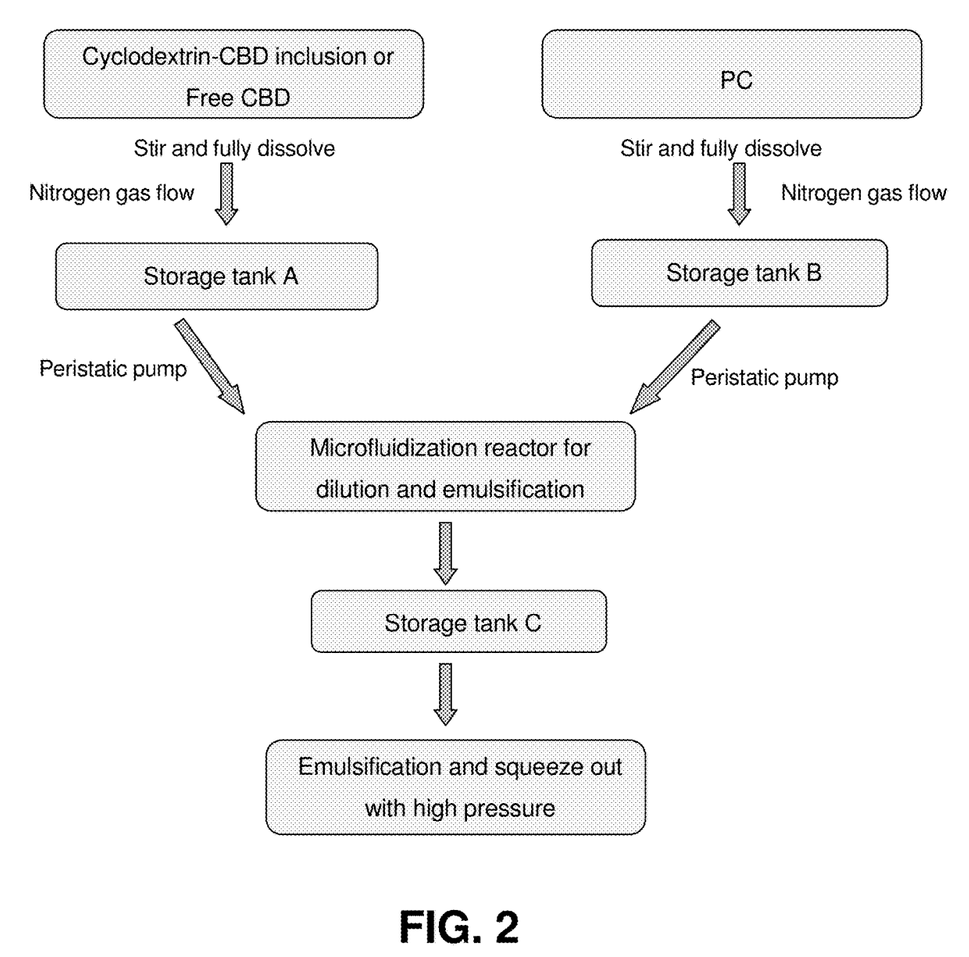
FIG. 2 is an illustrative flowchart showing method steps of preparing a dietary supplement composition according to second and third embodiments of the present invention.

As shown in FIG. 2, the method of preparing the dietary supplement composition includes the method steps of generating a cannabinoid phase by inclusion of cyclodextrin thereby creating cyclodextrin-CBD inclusion and by stirring the cyclodextrin-CBD inclusion in distilled water in a first container; generating a phospholipid phase by stirring a phospholipid compound, such as sunflower lecithin/sunflower lipid (PC), in distilled water in a second container; adding the cannabinoid phase and the phospholipid phase in vessel; performing a homogenizing step by mixing said cannabinoid phase and the phospholipid phase using a microfludizer (high pressure homogenization) at a temperature of about 55-65° C. so as to form a cannabinoid-phospholipid composition having a plurality of liposomal vesicles of the phospholipid, the liposomal vesicles having the cyclodextrin-CBD inclusion incorporated therein.

In such composition, the concentration of CBD ranges from 10% to 25%, and mostly is in the range of about 20% or more. In other words, ratio of concentration of CBD to the dietary supplement composition is about 1:5 or more. Such composition is 100% water soluble. It may be noted that in FIG. 2 only some of the method steps, and not all the method steps, are illustrated.

Optionally, one or more of rice bran, mannitol and trehalose may be added during any of above steps to the composition.

Figure 3:
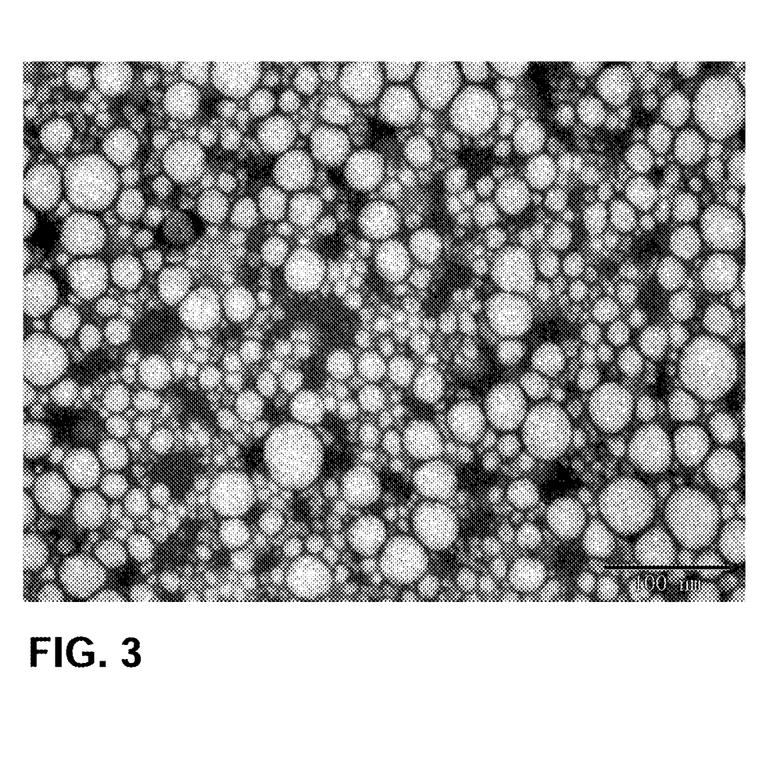
FIG. 3 is a TEM image of liposomal vesicles (nanoliposome) with cyclodextrin-CBD inclusion according to a second embodiment of the present invention.
Figure 5:
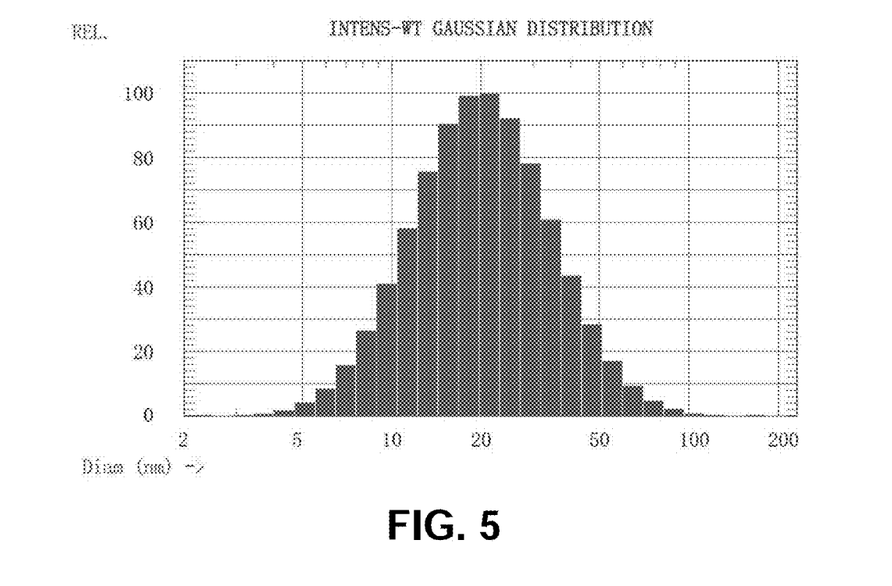
FIG. 5 is an intense-weight Gaussian distribution results for nanoliposomes of cyclodextrin-CBD inclusion sample according to a second embodiment of the present invention.

FIG. 3 is a transmission electron microscopy (TEM) image of nanoliposome with cyclodextrin-CBD inclusion according to the second embodiment of the present invention. The TEM image, as shown in FIG. 3, revealed spherical shapes of the liposomal vesicles, and substantially complete encapsulation of cyclodextrin-CBD inclusion in the liposomal vesicles. FIG. 5 shows liposomal vesicles size distribution results using Gaussian Distribution for cyclodextrin-CBD inclusion liposomal vesicles. Table 2 shown size distribution measurements for liposomes with cyclodextrin-CBD inclusion.

TABLE 2

Size distribution measurement for liposomes
with cyclodextrin-CBD inclusion

GAUSSIAN SUMMARY

| | |
|---|---|
| Mean Diameter: 23.1 nm | Variance (P.I.): 0.294 |
| Stnd. Deviation: 12.5 nm (54.2%) | Chi Squared: 1.346 |
| Norm. Stnd. Dev.: 0.542 (Coeff. of Var'n) | Baseline Adj.: 0.000% |
| | Z-Avg. Diff. Coeff.: 9.40E−008 cm2/s |

INSTRUMENT PARAMETERS

| | |
|---|---|
| Run Time: 0 Hr 2 Min 9 Sec | Wavelength: 639.0 nm |
| Count Rate: 317 KHz | Temperature: 23 deg C. |
| Channel #1: 16.6 K | Viscosity: 2.000 cp |
| Channel Width: 2.0 uSec | Index of Ref.: 1.333 |

The composition according to the second embodiment had a stability for two weeks at room temperature. The encapsulation efficiency is estimated close to 100%. No characteristic odor was sensed for the composition. TEM and light scattering data showed a mean size of 23 nm for both liposomes 23 nm, and a range of 10-60 nm. The size and distribution suggest good stability and rapid absorption. Viscosity is 2.0 cp, suggesting good compatibility with post-processing.

Third Embodiment

In a third embodiment, the main materials/ingredients used are (1) CBD, (2) distilled water, (3) sunflower lecithin, and (4) optionally, one or more of rice bran, mannitol and trehalose. In this embodiment, no cyclodextrin was added to the CBD. The CBD in this embodiment is also referred to as free CBD.

As shown in FIG. 2, the method of preparing the dietary supplement composition includes the steps of generating a cannabinoid phase by stirring the CBD (without additional agents, such as cyclodextrin, rice bran, mannitol and trehalose) in distilled water in a first container; generating a phospholipid phase by stirring a phospholipid compound, such as sunflower lecithin, in distilled water in a second container; adding the cannabinoid phase and the phospholipid phase in vessel; performing a homogenizing step by mixing said cannabinoid phase and the phospholipid phase using a microfludizer (high pressure homogenization) at a temperature of about 55-65° C. so as to form a cannabinoid-phospholipid composition having a plurality of liposomal vesicles of the phospholipid, the liposomal vesicles having the cyclodextrin-CBD inclusion incorporated therein. In such composition, the concentration of CBD ranges from 10% to 25%, and mostly is in the range of about 20% or more. In other words, ratio of concentration of CBD to the dietary supplement composition is about 1:5 or more.

Further, the cannabinoid-phospholipid composition may be subjected to method steps of emulsifying the cannabinoid-phospholipid composition, and squeezing out the cannabinoid-phospholipid composition at high pressure. Furthermore, the cannabinoid-phospholipid composition may be subjected to a method step of vacuum drying, spray drying and/or freeze drying to so as to make it in powder form.

Figure 4:
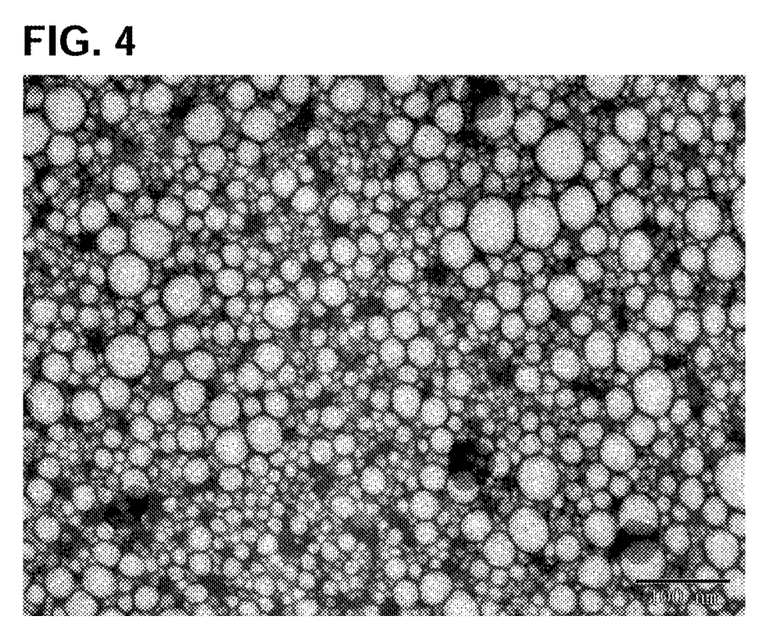
FIG. 4 is a TEM image of nanoliposome with free CBD according to a third embodiment of the present invention.
Figure 6:
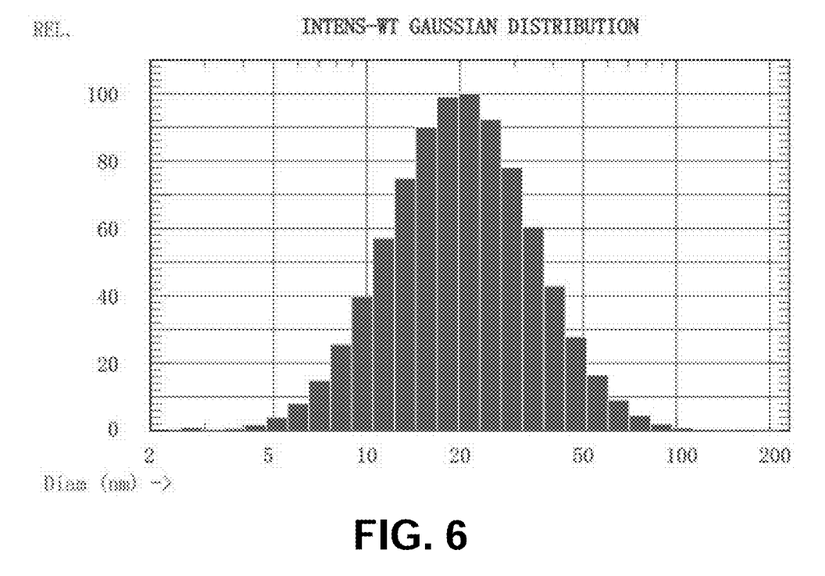
FIG. 6 is an intense-weight Gaussian distribution results for nanoliposomes of free CBD sample according to a third embodiment of the present invention.

FIG. 4 is a TEM image of nanoliposome with cyclodextrin-CBD inclusion according to the second embodiment of the present invention. The TEM image, as shown in FIG. 3, revealed spherical shapes of the liposomal vesicles, and complete encapsulation of free CBD in the liposomal vesicles. FIG. 6 shows liposomal vesicles size distribution results using Gaussian Distribution for free CBD liposomal vesicles. Table 3 shows size distribution measurements for liposomes with free CBD inclusion.

TABLE 3

Size distribution measurement (free CBD)

GAUSSIAN SUMMARY

| | |
|---|---|
| Mean Diameter: 23.2 nm | Variance (P.I.): 0.287 |
| Stnd. Deviation: 12.4 nm (53.6%) | Chi Squared: 1.170 |
| Norm. Stnd. Dev.: 0.536 (Coeff. of Var'n) | Baseline Adj.: 0.000% |
| | Z-Avg. Diff. Coeff.: 9.35E−008 cm2/s |

INSTRUMENT PARAMETERS

| | |
|---|---|
| Run Time: 0 Hr 1 Min 3 Sec | Wavelength: 639.0 nm |
| Count Rate: 319 KHz | Temperature: 23 deg C. |
| Channel #1: 8.0 K | Viscosity: 2.000 cp |
| Channel Width: 2.0 uSec | Index of Ref.: 1.333 |

The composition, according to the third embodiment, had a stability for two weeks at room temperature. The encapsulation efficiency is estimated close to 100%. No characteristic odor was sensed for the composition. TEM and light scattering data showed a mean size of 23 nm for both liposomes 23 nm, and a range of 10-60 nm. The size and distribution suggest good stability and rapid absorption. Viscosity is 2.0 cp, suggesting good compatibility with post-processing.

The dietary supplement compositions, including CBD formulations of the present invention, may be made available in powder, table, capsule, gummies, gel, or liquid form for ingesting by humans and animals.

The present invention has been described herein with respect to specific illustrative embodiments, the foregoing description is intended to illustrate, rather than to limit the invention. Those skilled in the art will realize that many modifications of the illustrative embodiment could be made which would be operable. All such modifications, which are within the scope of the claims, are intended to be within the scope and spirit of the present invention.

What is claimed is:

1. A dietary supplement composition comprising a dispersion including a plurality of liposomal vesicles, said dietary supplement composition comprising
   a hydrophobic nutrient comprising at least one of cannabinoid and mixtures of cannabinoids;
   one or more of rice bran extract, mannitol and trehalose; and
   phospholipid contained in said liposomal vesicles;
   wherein said hydrophobic nutrient is incorporated within said liposomal vesicles;
   wherein said dispersion is generated by using a homogenizer;
   wherein said hydrophobic nutrient is in the amount ranging from about 10 mass % to 25 mass % in said dispersion; and
   said dispersion is water soluble.

2. A dietary supplement composition according to claim 1, wherein said phospholipid comprises sunflower lecithin.

3. A dietary supplement composition according to claim 1, further comprises one or more of α-cyclodextrin, β-cyclodextrin, and γ-cyclodextrin.

4. A dietary supplement composition according to claim 1, wherein size of liposomal vesicles ranges from 10-60 nm.

5. A dietary supplement composition according to claim 1, wherein average size of liposomal vesicles is about 23 nm.

6. A dietary supplement composition according to claim 5, wherein said hydrophobic nutrient is in the amount ranging from about 20 mass % to 25 mass % in said dispersion.

7. A dietary supplement composition according to claim 1, wherein said composition is provided in a formulation selected from the group consisting of a capsule, a powder, a tablet, a liquid, an emulsion, a gel, a gummy, a beverage and a functional food.

8. A method of preparing a dietary supplement composition, said method comprising the steps of:
generating a cannabinoid phase by stirring an active ingredient comprising one or both of cannabinoid and cannabinoid compound in a first container;
generating a phospholipid phase by stirring a phospholipid compound in a second container;
adding said cannabinoid phase and said phospholipid phase in vessel;
performing a homogenizing step by mixing said cannabinoid phase and said phospholipid phase for a predetermined time so as to form a cannabinoid-phospholipid composition having a plurality of liposomal vesicles of said phospholipid compound, said liposomal vesicles having said one or both the cannabinoid and cannabinoid compound incorporated therein;
wherein a concentration of said one or both the cannabinoid and cannabinoid compound incorporated in said liposomal vesicles in said cannabinoid-phospholipid composition is about 10 mass % to 25 mass %; and
wherein the method step of generating the cannabinoid phase by stirring the active ingredient comprises the step of adding at least one of α-cyclodextrin, β-cyclodextrin, and γ-cyclodextrin to said active ingredient.

9. A method of preparing a dietary supplement composition according to claim 8, wherein the method step of generating the cannabinoid phase by stirring the active ingredient comprises the step of adding at least one of rice bran extract, mannitol and trehalose.

10. A method of preparing a dietary supplement composition according to claim 8, further comprises the step of emulsifying of said cannabinoid-phospholipid composition.

11. A method of preparing a dietary supplement composition according to claim 8, further comprises the step of squeezing out said cannabinoid-phospholipid composition.

12. A method of preparing a dietary supplement composition according to claim 8, wherein size of said liposomal vesicles is in a range of 10-60 nm.

13. A method of preparing a dietary supplement composition according to claim 8, wherein average size of said liposomal vesicles is about 23 nm.

14. A method of preparing a dietary supplement composition according to claim 8, wherein viscosity of said cannabinoid-phospholipid composition is about 2.0 cp.

15. A method of preparing a dietary supplement composition, said method comprising the steps of:
generating a cyclodextrin-cannabinoid phase by kneading cannabinoid oil mixed with a cyclodextrin and distilled water;
rolling the cyclodextrin-cannabinoid phase into a plurality of cylindrical rolls;
storing said cylindrical rolls of said cyclodextrin-cannabinoid phase at ambient temperature for a period of about 24 hours;
adding distilled water to the cylindrical rolls of said cyclodextrin-cannabinoid phase,
performing a first homogenizing step by mixing distilled water and said cylindrical rolls of the cyclodextrin-cannabinoid phase using a homogenizer operated at progressively increasing speeds from about 8000 rpm to 100000 rpm for a time period of about 90 minutes so as to form a cyclodextrin-cannabinoid composition;
adding an additional ingredient selected from the group consisting of a rice bran, mannitol and trehalose to said cyclodextrin-cannabinoid composition;
performing a second stage of homogenizing said additional ingredient and said cyclodextrin-cannabinoid composition using a homogenizer operated at progressively increasing speeds from about 8000 rpm to 10,0000 rpm for a time period of about 90 minutes so as to form a cyclodextrin-cannabinoid-additional ingredient mixture;
adding phospholipid compound to said cyclodextrin-cannabinoid-additional ingredient mixture; and
performing a third stage of homogenization by blending of a mixture of said phospholipid compound and said cyclodextrin-cannabinoid-additional ingredient mixture by using a homogenizer so as form a cannabinoid-cyclodextrin-cannabinoid-additional ingredient-phospholipid composition having a plurality of liposomal vesicles of said phospholipid compound, said liposomal vesicles having said cyclodextrin-cannabinoid composition incorporated therein;
wherein said liposomal vesicles have coating of said additional ingredient formed around said liposomal vesicles.

16. A method of preparing a dietary supplement composition according to claim 15, wherein the first homogenizing step and the second homogenizing step are performed at a temperature between 55-65° C.

17. A method of preparing a dietary supplement composition according to claim 15, wherein said phospholipid compound is sunflower lecithin.

18. A method of preparing a dietary supplement composition according to claim 15, wherein a cannabinoid-additional ingredient-phospholipid composition comprises said cannabinoid oil in the amount of about 19-20 mass %, said cyclodextrin in the amount of about 68-67 mass %, said phospholipid compound in the amount of about 11-12 mass %, and said additional ingredient in the amount of about 0-1 mass %.

* * * * *